May 16, 1950 W. B. CLARKE Plant Pat. 941
FLOWERING QUINCE PLANT
Filed June 13, 1949
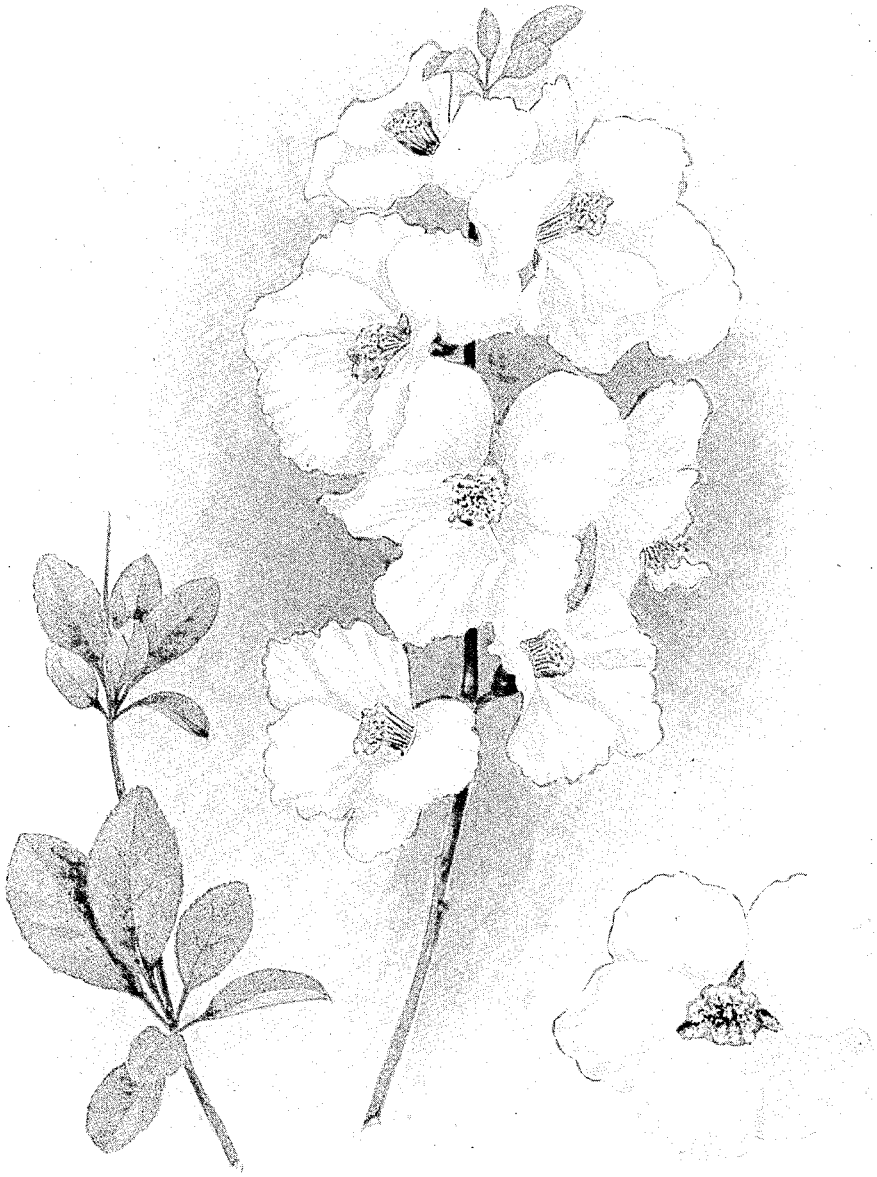
WITNESS
Addison J. Avery
INVENTOR
WALTER BOSWORTH CLARKE,
by Rummler & Rummler & Snow,
ATTYS Patented May 16, 1950

UNITED STATES PATENT OFFICE

941

FLOWERING QUINCE PLANT

Walter Bosworth Clarke, San Jose, Calif., assignor to W. B. Clarke & Co., San Jose, Calif., a partnership Application June 13, 1949, Serial No. 98,764

1 Claim. (Cl. 47—60)

My present discovery relates to a new and distinct variety of flowering quince plant. The parentage is unknown but it can be classed as a horticultural variety of *Chaenomeles lagenaria* (Koidzumi). It is the result of definite breeding efforts carried on by me since 1931. This new variety has been asexually reproduced at Santa Clara County, California, by grafting and its characteristics appear to be permanently fixed.

The characteristics which distinguish this new variety from other varieties are the large size of its flowers, their intense red coloring, their overlapping of the petals, and their ruffled edges.

The accompanying painting shows in full color a single stem with a characteristic group of flowers with separate views showing leaf formation and a face view of a single flower.

The highly distinctive feature of this new variety is the ruffled marginal portions of the flower petals, which is a very unusual characteristic of flowering quinces. Another distinguishing characteristic of this new variety is the deep red coloring of the flowers, which open as a geranium red and deepen with age to a blood red.

The plant is a vigorous grower, erect, and blooms very freely in midseason.

In general plant structure, this new variety of quince plant is similar to the well-known Lagenaria and Superba groups. Its habit of growth is vigorous, erect and only moderately spreading. With age it will attain a height of about eight feet. Its leaves are of the usual shape and size, of a pleasing green in color, and of a sufficient quantity to make an effective background for the brilliant coloring of the flowers. The only variety comparable to this new variety is one called "Blood Red," but this new variety is more vivid red in color.

The following is a detailed description of my new variety:

Parentage: Seedling.
*Seed and pollen parents.*—Unknown.
Classification: *Chaenomeles lagenaria* (Koidzumi).

*Plant*

Form: Bush.
Height: About 8 feet with age.
Growth: Very vigorous and erect and only moderately spreading.
Hardy: Yes.

Foliage:
*Color.*—New foliage: soft green; old foliage: deep green.
Thorns: None on young plants; may develop some as plant gets older.

*Flowers*

Blooms: At least once, and very profusely.
Size: Large.
Petalage: 5.
*Form.*—Almost round with ruffled margins.
*Color.*—Blood red. Outside and inside of petals are a solid red color.
Discoloration: No change except color deepens with age.
Appearance: Velvety.
Disease resistance: Apparently perfectly resistant.
Lasting quality: On plant good.

The colors of the flower petals are defined in the following list according to the Horticultural Color Chart of the British Horticultural Society and those of the foliage and stem according to Maerz & Paul's Dictionary of Color:

Lightest red—Geranium Lake, H. C. C., 20/–
Darkest red—Blood Red, H. C. C., 820/2
Leaf top green, M. & P., Plate 21–L–6
Leaf bottom green, M. & P., Plate 21–J–5
Stem, M. & P., Plate 56–H–2

This new variety is easily distinguished from other varieties by the rich and brilliant red coloring of the flowers, and their broad petals with overlapping side margins and wavily ruffled outer end margins which is an unusual characteristic of the flowering quince. In many other respects this variety resembles flowering quince plants of the Superba and Lagenaria groups.

Having thus disclosed my invention, I claim:

A new and distinct variety of flowering quince plant, substantially as illustrated and described, characterized particularly by the intense red coloring of the flowers; the broad overlapping petals with ruffled outer marginal end portions; the erect vigorous growth of the bush; and its profuse midseason blooming.

WALTER BOSWORTH CLARKE.

No references cited.